US012575886B2

(12) United States Patent
Junio

(10) Patent No.: US 12,575,886 B2
(45) Date of Patent: Mar. 17, 2026

(54) INTRAOPERATIVE ROD GENERATION BASED ON AUTO IMPLANT DETECTION

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 1139 days.

(21) Appl. No.: 17/491,014

(22) Filed: Sep. 30, 2021

(65) Prior Publication Data

US 2022/0117664 A1 Apr. 21, 2022

Related U.S. Application Data

(60) Provisional application No. 63/092,662, filed on Oct. 16, 2020.

(51) Int. Cl.

| | |
|---|---|
| *A61B 34/10* | (2016.01) |
| *A61B 17/70* | (2006.01) |
| *G06T 7/70* | (2017.01) |
| *G16H 20/40* | (2018.01) |
| *G16H 30/20* | (2018.01) |
| *G16H 30/40* | (2018.01) |
| *G16H 50/20* | (2018.01) |
| *G16H 50/50* | (2018.01) |
| *A61B 34/30* | (2016.01) |
| *G16H 40/67* | (2018.01) |

(52) U.S. Cl.
CPC .......... *A61B 34/10* (2016.02); *A61B 17/7011* (2013.01); *G06T 7/70* (2017.01); *G16H 20/40* (2018.01); *G16H 30/20* (2018.01); *G16H 30/40* (2018.01); *G16H 50/20* (2018.01); *G16H 50/50* (2018.01); *A61B 2034/104* (2016.02); *A61B 2034/108* (2016.02); *A61B 34/30* (2016.02); *G06T 2207/20081* (2013.01); *G06T 2207/30012* (2013.01); *G06T 2207/30052* (2013.01); *G16H 40/67* (2018.01)

(58) Field of Classification Search
None
See application file for complete search history.

(56) References Cited

U.S. PATENT DOCUMENTS

| | | | |
|---|---|---|---|
| 7,957,831 B2 | 6/2011 | Isaacs | |
| 9,655,649 B2 | 5/2017 | Shoham | |
| 10,188,480 B2 | 1/2019 | Scholl et al. | |
| 10,405,935 B2 * | 9/2019 | McGahan | A61B 34/20 |
| 10,631,907 B2 | 4/2020 | Zucker et al. | |
| 2018/0303552 A1 * | 10/2018 | Ryan | A61B 17/7002 |
| 2019/0231435 A1 * | 8/2019 | Zucker | A61B 17/7077 |
| 2020/0129240 A1 | 4/2020 | Singh et al. | |

FOREIGN PATENT DOCUMENTS

| | | |
|---|---|---|
| WO | WO 2017/064719 | 4/2017 |
| WO | WO 2017/221257 | 12/2017 |
| WO | WO 2018/131044 | 7/2018 |
| WO | WO 2018/131045 | 7/2018 |
| WO | WO 2019/102473 | 5/2019 |
| WO | WO 2020/079598 | 4/2020 |

OTHER PUBLICATIONS

Qureshi et al. in Journal of AAOS vol. 22(12):800-809.*
Chang et al. (Frontiers in Surgery (Aug. 2020) vol. 7, Article 54:15 pages).*

* cited by examiner

*Primary Examiner* — Lori A. Clow
(74) *Attorney, Agent, or Firm* — Sheridan Ross P.C.

(57) ABSTRACT

A method and system for improving spinal alignment parameters of a subject, by planning the shape of an intervertebral rod for attaching to previously implanted hardware whose positions and orientations are known from intraoperative images. Once the planned shape of the rod has been prepared, determining if, when attached to the inserted hardware, a spine configuration is achieved having acceptable values of selected spinal alignment parameters. If not, the shape of the rod is amended iteratively, until the selected spinal alignment parameters have acceptable values with attachability to the implanted hardware. If, after a predetermined number of iterations, the amended shape of the rod still does not achieve acceptable values of spinal alignment parameters, while maintaining attachability to the implanted hardware, performing a spinal manipulation procedure on at least one vertebra of the spine to increase the attachability of the rod to the implanted hardware.

19 Claims, 5 Drawing Sheets

INTRAOPERATIVE ROD GENERATION BASED ON AUTO IMPLANT DETECTION

CROSS REFERENCE TO RELATED APPLICATIONS

This application claims priority to U.S. Provisional Application No. 63/092,662, filed on Oct. 16, 2020, and entitled "Intraoperative Rod Generation Based on Auto Implant Detection", the entirety of which is hereby incorporated by reference.

FIELD

The present disclosure relates to the field of spinal surgery, especially using a system and methods for optimizing intervertebral rods for minimally invasive insertion.

BACKGROUND

In surgical procedures to correct vertebral pathology, operations are often performed using a fixating intervertebral rod or set of rods that holds the spinal column in its desired location over time. The intervertebral rods are secured by a series of pedicle screws that are inserted into the pedicles of vertebrae in the region of surgical interest. Fusion of vertebrae may be performed for correction of scoliosis or kyphosis, or for facet joint-related pain, to stabilize a previous laminectomy, or other indications.

Following development of a strategy for obtaining the desired vertebral correction, the surgeon needs to plan a rod that will correct the patient's vertebral pathology. Planning the rod such that it may be inserted in a minimally invasive way may differ from planning a rod that is to be inserted in an open procedure. Either way, the rod must be physically bent to conform to the shape of the planned rod.

Historically, rods were bent manually by the surgeon without pre-operative or intra-operative planning, in an estimation of the shape needed for the desired outcome and without an accurate knowledge of the actual spatial location of the screws or other implants within the spine. Even when preoperative planning of rod shape is used, the inserted pedicle screws or other hardware may change location or orientation after placement and before rod insertion, due to surgical spinal manipulations, such as bony decompression and interbody insertion. The shape of each rod must be designed to account for the patient's natural vertebral curvature, the planned correction to the curvature to improve the patient's posture and his/her ability to carry out activities of daily living.

A more sophisticated method of planning rod shaping involves an optical navigation-based approach to evaluate the location of the screw heads, or a hand-held touch probe tracked by a navigation system. Yet several embodiments of the present disclosure provide various improvements over those approaches. As discussed below in more detail, some embodiments accurately detect and measure the location of each screw in its entirety, which provides greater accuracy than approaches that identify only the top of the screw, leaving the screw angle unknown. Still other embodiments account for screw tulip hubbing, which further increases the accuracy of screw identification. These advantages are particularly valuable in minimally invasive surgical procedures (MIS), where screws are harder to accurately detect due to the slim insertion point of the tracked navigation tool and the presence of intervening soft tissue.

Thus, these improvements and others discussed herein improve intra-operative rod bending and thereby improve surgical outcomes and minimize time spent in the operating room. In MIS cases, for example, embodiments discussed herein enable the creation of a rod that is both possible and easy to insert into the implanted screws heads with a minimal investment of time and effort.

Systems for minimally invasive spinal fusion and minimally-invasive rod insertion have been described in the following patents and patent applications, co-owned by the present applicant, each of which is fully incorporated herein by reference:

U.S. Pat. No. 9,655,649 for "Minimally Invasive Spinal Fusion",

WO 2017/221257 for "Minimally Invasive Intervertebral Rod Insertion",

WO 2017/064719 for "Global Spinal Alignment Method",

U.S. application Ser. No. 15/533,037 for "Shaper for Vertebral Fixation Rods" and WO 2019/102473 for "Spatial Hard Tissue Update Based on Implant Images".

The disclosures of each of the publications mentioned in this section and in other sections of the specification, are hereby incorporated by reference, each in its entirety.

SUMMARY

Rod planning that takes into consideration the accurate knowledge of the pose of inserted screws, and/or the change of the pose resulting from spinal manipulation, would be beneficial to the surgeon by reducing time spent on rod insertion, or even having to turn the procedure into an open operation. In cases where a rod was planned prior to the procedure, the planned shape may still not be aligned precisely with the alignment of the vertebrae intraoperatively. In cases involving removal of herniated disk or bone spurs and/or interbody insertion, surgical manipulations may cause the spine to shift or reposition in a way that is hard to predict precisely prior to carrying out the surgical steps prior to rod insertion. Shifts in anatomical structures may take place during the operation. Thus, a solution that could provide such intra-operative data, such as some of the embodiments discussed herein, would enable the surgeon to generate a more suitable rod construct.

Embodiments of the present disclosure provide new systems for optimizing the planned fit between an intervertebral rod and the previously inserted pedicle screws to which the rod is to be attached, as initially determined in a preoperative plan. Methods described in this disclosure use an image processing routine to detect the pose of pedicle screws in intra-operative images, and then use this information in planning and constructing a rod of the desired shape for insertion in a specific patient. Rather than relying on a registration process, which use preoperative and intraoperative images to associate the preoperatively planned screw positions with the real life expected position, or alternatively using a touch probe/sensor to identify the screw heads after insertion, some embodiments of the present disclosure use an image-processing routine to distinguish the implanted screws from the vertebral pedicles into which they have been inserted, based on images acquired intraoperatively following screw insertion. This method enables identification of both position and orientation of each screw relative to the surrounding bony anatomy. As the actual, detected position and orientation of each implanted screw may differ from that shown in the preoperative plan, collection of amended three-dimensional positional information regarding the implanted screws, enables the system or the surgeon to update the planned shape of the rod prior to insertion. This modification of the planned rod is designed to generate a shape that will more accurately fit into the actual position and orientation of the tulips of the pedicle screws. The amended rod shape also maintains the desired correction of spinal alignment parameters based on the detected screw positions, thus enabling a rod shape that both accurately fits into the screw tulips, and enables the desired correction of vertebral pathology and spinal alignment parameters.

The images from the preoperative plan with the planned screw positions, on the basis of which the initial rod shape was planned, can be digitally compared with the intraoperative images having the detected screw positions and orientations, into which the rod shape to be used must fit. Since the preoperative images are used only for planning the screw positions and the rod shape, once the screws have been inserted, those preoperative images need no longer be related to, and, unlike prior art methods in this field, there is no need to register intraoperatively obtained images with preoperatively obtained images. The method extracts the implanted position and orientation of the screws, as well as the vertebral alignment, directly from the obtained intraoperative images. It then compares this information with the preoperatively planned rod shape to determine compatibility between the virtual, planned rod and the actual, detected screw positions and orientations. Thus, the purpose of the intraoperative three-dimensional image is to identify the actual screw position, in order to update the planned shape of the rod. In some embodiments, the actual position and orientation of the screws may be used in order to optimize the surgical outcome by reducing the number and degree of surgical manipulations.

In a typical spinal fusion operation, if indicated by the preoperative plan after screw insertion, manual or surgical spinal manipulation may be done to align the vertebral column in a manner that corrects the spinal alignment parameters. Rod insertion is then accomplished gradually, such that the corrections to the vertebral alignment are fixed in place as the rod is attached to the screws, generally securing the screws at either end of the rod and working toward the middle of the spinal column. Especially in a spinal fusion involving instrumentation of multiple, and possibly, quite distant vertebral levels, thus requiring rods of many centimeters' length, the variation between the preoperative plan and the actual implanted screw positions may reach several millimeters. This difference is surgically significant, and may make the original planned rod difficult or impossible to insert in its initial shape. By using the method of the current disclosure to identify the exact position and orientation of the implanted screws prior to shaping and inserting the rod, it is possible to update the shape of the rod to enable a better surgical outcome.

The process of adjustment of planned rods or other hardware to be inserted may be performed iteratively. Iterative processing may be needed to optimize spinal alignment in conjunction with the amendments of rod shape to match screw head positions, or in the case that further surgical steps are performed after acquisition of the intraoperative images.

An additional benefit of the embodiments of the present disclosure is that the information acquired from the intraoperative images regarding actual screw position may be provided to the controller of a surgical robotic system. Changes in pedicle screw position, orientation, number, and location, may result in difficulty carrying out the operation according to the preoperative plan, and the system may thus be programmed to amend the preoperative plan according to changes in these parameters.

A goal of some embodiments of the present disclosure is to enable construction and insertion of one or more optimally shaped intervertebral rods in a minimally invasive procedure for spinal instrumentation. In a minimally invasive procedure, the system calculates both the optimal shape of the rod for correcting a vertebral deformity, as well as angles of curvature that allow for inserting the rod through the implanted pedicle screw heads in a minimally-invasive manner. These two goals may be competing, in that the optimal rod shape for correction of the vertebral pathology may not be both insertable through a single opening, and shaped such that it is manipulatable through each pedicle screw head. This is because the preferred rod may be curved in a manner that makes it difficult to wend through a particular path. Consequently, motion planning procedures can be employed, such as, for instance, the algorithm known as the piano movers' problem. Stated differently, a path-finding algorithm may be incorporated into the method for updating the planned rod shape according to the detected positions of the implanted screws on intraoperative images. Both a path-finding algorithm and a hardware-detection algorithm may be incorporated into the method, along with a means of balancing the constraints of the rod shape with the desired corrected spinal alignment parameters, if correction of scoliosis, kyphosis, kyphoscoliosis, or other vertebral pathology is a goal of the specific operation. Bending a metal rod to less than a certain radius of curvature results in weakness of the metal at the point of bending. The system balances the needs of introducing sufficient curvature to the rod to optimally correct the spinal alignment parameters, with the need to prevent bending beyond a curvature that would result in unacceptable weakening of the material of which the rod is composed.

One advantage of certain embodiments of the present disclosure is that image registration is not required. The intraoperative three-dimensional image, or set of two-dimensional images acquired from different angles, of the vertebral column and the implanted pedicle screws, show both of these elements in direct three-dimensional relationship to each other. These embodiments may also identify the position and orientation of each screw, through whose head the intervertebral rod is to be inserted or to which it is to be attached. A preoperative plan will have determined the optimum rod shape, according to the planned position of the screws prior to insertion. However, once implanted, the screw position and location may differ from the preoperative plan, either because the surgeon decided intraoperatively to alter an aspect of the instrumentation, or because of expected or unexpected anatomical findings, necessitating performance of a surgical manipulation to adjust the spinal curvature to achieve the desired correction of spinal alignment parameters. The actual, detected screw positions on the intraoperative image may differ from the planned positions of the preoperative plan, either because of these spinal manipulations or because of incidental aberrations in the screw placements. In either eventuality, embodiments of the method enable the planned shape of the rod to be amended according to the actual screw positions.

Therefore, with some embodiments, there is a preference to deliver an intra-operative implant location solution for inserting a rod preferably in a minimally invasive procedure, and if not, then in an open operation, that will enable creation of an accurately-shaped rod, given the actual location of the implants and allowing for computed optimization of the rod based on that information.

In some embodiments, during development of certain embodiments of the disclosed system, an image-processing subroutine, function, or algorithm is created or pre-conditioned to detect a variety of implants composed of differently available materials. The algorithm may be pre-conditioned, such that the function is trained or taught during the developmental stage of the creation of the routines necessary for executing the methods of the present disclosure. Alternately or in addition, the algorithm may be used during operation of the system, such that the accuracy of performance improves over time depending on the patient base being treated by a given system. In the case of an image-processing routine for detecting screw position and orientation, the routine learns to identify and distinguish the hardware implant from the surrounding bony tissue. In many cases, the implants will be pedicle screws; however, any type of metal or other hardware used in spinal procedures could also be detected by the method. The method detects different types of implants, independently of the material of which the implant is comprised, whether titanium, steel, silicone, or any other material typically used for surgical implants.

In embodiments in which the pre-conditioning is performed during development of the system, each system will have the same accuracy and output in implanted hardware detection. However, in further implementations, the method algorithm may be programmed to continue learning after being put into clinical use. In such a case, each product or system in operation may use a slightly different means of accomplishing the same final rod shape and fit of the rod into the implanted screws, based on its learning experience with each patient and surgeon, and the outcome of each operation, in comparison with the outcomes of similar operations whose results are stored in a large database. Such advanced learning would necessitate that the system be provided with post-operative imaging studies and other clinical data.

The planning procedure, according to some embodiments, involves a compromise among a number of different factors, including:

the need for maintaining minimal forces on the pedicle screws, and hence on their associated vertebrae, to reduce the possibility of rod breakage or screw pull-out;

the need to provide an acceptable curvature correction that relieves the patient's condition sufficiently;

the ability to perform the entire procedure minimally invasively; and the minimization or complete elimination of the need for osteotomies, if suitable spinal alignment parameters can be achieved without such a procedure.

There is thus provided in accordance with an implementation of the devices described in this disclosure, a system for optimizing a planned shape of an intervertebral rod for improving spinal alignment parameters of a subject, the system comprising:

at least one processor executing instructions stored on at least one non-transitory storage medium, to cause the at least one processor to:

(a) receive at least one intraoperative image comprising at least a region of the spine containing implanted hardware to which the intervertebral rod is to be attached, and, from at least one intraoperative image, detecting the position and orientation of the implanted hardware;

(b) if the detected positions and orientations of the implanted hardware are incompatible with a planned shape of the intervertebral rod, change the planned shape of the intervertebral rod so as to increase compatibility with the detected positions and orientations of the implanted hardware;

(c) determine if the intervertebral rod having the changed planned shape obtained in step (b), would, if attached to the inserted hardware, achieve a spine configuration having acceptable values of selected spinal alignment parameters;

(d) if the changed planned shape of the intervertebral rod obtained in step (b) does not achieve acceptable values of the selected spinal alignment parameters, further change the planned shape of the intervertebral rod towards achieving acceptable values of the selected spinal alignment parameters;

(e) determine if an intervertebral rod having the planned shape provided in step (d) maintains compatibility with the implanted hardware, and if not, repeating steps (b) to (e); and (f) if the planned shape of the rod provided in step (d) does not achieve acceptable values of the selected spinal alignment parameters while maintaining compatibility with the implanted hardware, provide a recommendation for a spinal manipulation procedure on at least one vertebra of the spine of the subject to improve the spinal alignment parameters of the subject.

In various implementations of the system for optimizing a planned shape of an intervertebral rod for improving spinal alignment parameters of a subject, factors may be modified, as specified herewithin below. The changing of the planned shape of the rod may be performed in at least one of the sagittal and the coronal planes of the spine of the subject. Any of the planned shapes of the intervertebral rod may allow the shaped rod to be attached to the implanted hardware components by insertion through a single opening in the subject in a minimally invasive procedure. At least some of the implanted hardware may comprise pedicle screws. The planned rod shape may be changed using a path planning algorithm. A radius of curvature of any bends in any plans for the intervertebral rod may be limited to being greater than a predetermined level. The predetermined minimum level of the radius of curvature is determined such that the strength of the intervertebral rod does not fall below a predetermined limit. Changing the planned shape of the rod in step (b) may be performed only if the intervertebral rod cannot be attached to the implanted hardware without applying more than a predetermined level of force to at least one of the rod and a screw to which the rod is to be attached.

The spinal alignment parameters may comprise at least one of spinal vertical axis (SVA), lumbar lordosis (LL), thoracic kyphosis (TK), pelvic tilt (PT), pelvic incidence (PI), (PI-LL), and the sagittal pelvic angle (T1 slope). The step of detecting the position and orientation of the implanted hardware can be performed on implanted hardware comprising titanium, steel, silicone, or other material used for surgical implants.

The implanted hardware position and orientation may be detected by use of an image-processing routine, which may be trained using one of machine learning or other form of artificial intelligence to distinguish the implanted hardware from the surrounding bony tissue. The image-processing routine training may be performed either prior to routine clinical operation of the system or continuously during post-sales operation of the system. The system may be configured such that step (f) is performed after a predetermined number of iterations of steps (b) to (e).

There is thus provided in accordance with an implementation of the devices described in this disclosure, a method for improving spinal alignment parameters of a subject, comprising:

(a) receiving at least one intraoperative image comprising at least a region of the spine of the subject where spinal alignment hardware is implanted, and detecting positions and orientations of the implanted hardware to which an intervertebral rod is to be attached;

(b) changing a planned shape of the intervertebral rod so as to facilitate attachment to the implanted hardware;

(c) verifying that the intervertebral rod having the changed planned shape obtained in step (b), would, if attached to the implanted hardware, achieve a spine configuration having acceptable values of selected spinal alignment parameters;

(d) if the changed planned shape of the intervertebral rod obtained in step (b) does not achieve acceptable values of the selected spinal alignment parameters, further changing the planned shape of the rod towards achieving acceptable values of the selected spinal alignment parameters; and (e) determining that the rod having the changed planned shape provided in step (d) maintains attachability to the implanted hardware, and if not, repeating steps (b) to (e)];

wherein a final planned shape of the rod achieves acceptable values of the selected spinal alignment parameters while maintaining attachability to the implanted hardware.

In various implementations of the method for improving spinal alignment parameters of a subject, factors may be modified, as specified herewithin below. If, after a predetermined number of iterations of steps (b) to (e), the final planned shape of the rod does not achieve acceptable values of the selected spinal alignment parameters while maintaining attachability to the implanted hardware, a step may be added of performing a spinal manipulation procedure on at least one vertebra of the spine of the subject to increase the attachability of the rod to the implanted hardware. Steps (a) to (f) may be repeated until the spinal alignment parameters of the subject have acceptable values, within the constraint of the intervertebral rod being attachable to the implanted hardware. Changing the planned shape of the rod may be performed in at least one of the sagittal and the coronal planes of the spine of the subject, and the planned shape may be changed using a path planning algorithm. The planned shape of the intervertebral rod may allow the shaped rod to be attached to the implanted hardware components by insertion through a single opening in the subject in a minimally invasive procedure. At least some components of the implanted hardware may comprise pedicle screws. A radius of curvature of any bends planned in the intervertebral rod, may be limited to being greater than a predetermined level. The predetermined minimum level of the radius of curvature may be determined such that the strength of the intervertebral rod does not fall below a predetermined limit. Changing the planned shape of the rod in step (b) may only need be performed if the intervertebral rod cannot be attached without applying more than a predetermined level of force to at least one of the rod and the screw to which the rod is to be attached. The spinal alignment parameters may comprise at least one of spinal vertical axis (SVA), lumbar lordosis (LL), thoracic kyphosis (TK), pelvic tilt (PT), pelvic incidence (PI), (PI-LL), and the sagittal pelvic angle (T1 slope). The method may be able to detect implanted hardware composed of titanium, steel, silicone, or any other material used for surgical implants. The implanted hardware position and orientation may be detected by use of an image-processing routine. The image-processing routine may be trained using one of machine learning or other form of artificial intelligence to distinguish the implanted hardware from the surrounding bony tissue. The image-processing routine training may be performed prior to routine clinical operation of the system or continuously during post-sales operation of the system.

There is thus further provided in accordance with an implementation of the devices described in this disclosure, a system for optimizing a planned shape of an intervertebral rod to be attached to inserted hardware during a minimally invasive procedure, the system comprising:

at least one processor executing instructions stored on at least one non-transitory storage medium, to cause the at least one processor to:

(a) detect in at least one intra-procedural image, positions and orientations of implanted hardware to which the intervertebral rod is to be attached;

(b) determine if the detected positions and orientations of implanted hardware permit the intervertebral rod to be inserted minimally invasively;

(c) if the detected positions and orientations of the implanted hardware do not permit the intervertebral rod to be inserted minimally invasively, amend the planned shape of the intervertebral rod such that the intervertebral rod can be inserted and attached minimally invasively;

(d) determine if the intervertebral rod having the amended planned shape obtained in step (c), would, if attached to the implanted hardware components, achieve a spine configuration having acceptable values of selected spinal alignment parameters;

(e) if the amended planned rod shape obtained in step (c) is not compatible with acceptable values of the selected spinal alignment parameters, further amend the planned shape of the rod iteratively to accomplish the desired spinal alignment parameter;

(f) if the further amended rod shape does not allow desired correction of the spinal alignment parameters through a minimally invasive rod insertion procedure, provide a recommendation to amend the surgical plan.

In various implementations of the system for optimizing a planned shape of an intervertebral rod to be attached to inserted hardware during a minimally invasive procedure, factors may be modified, as specified herewithin below. Amending or further amending the planned shape of the intervertebral rod may allow the shaped rod to be attached to the implanted hardware through a single incision. The implanted hardware may comprise pedicle screws. The system may further comprise use of a path planning algorithm for determining whether the amended planned rod can be inserted through a single incision. The recommendation to amend the surgical plan may comprise converting the intended minimally invasive procedure into an open operation or may comprise a spinal manipulation. Steps (c) through (e) may be repeated a predetermined number of iterations before proceeding to step (f).

There is thus further provided in accordance with an implementation of the devices described in this disclosure, a method for optimizing a planned shape of an intervertebral rod for improving spinal alignment parameters of a subject, the method comprising:

(a) receiving at least one intraoperative image comprising at least a region of the spine containing implanted hardware to which the intervertebral rod is to be attached, and, from at least one intraoperative image, detecting the position and orientation of the implanted hardware;

(b) changing the planned shape of the intervertebral rod so as to increase compatibility with the detected positions and orientations of the implanted hardware;

(c) determining if the intervertebral rod having the changed planned shape obtained in step (b), would, if attached to the inserted hardware, achieve a spine configuration having acceptable values of selected spinal alignment parameters;

(d) updating the planned shape of the intervertebral rod to maintain compatibility with the implanted hardware and achieve acceptable values of the selected spinal alignment parameters; and (e) if the planned shape of the rod provided in step (d) does not achieve acceptable values of the selected spinal alignment parameters while maintaining compatibility with the implanted hardware, providing a recommendation for a spinal manipulation procedure on at least one vertebra of the spine of the subject to improve the spinal alignment parameters of the subject.

There is thus provided in accordance with an implementation of the devices described in this disclosure, a system for optimizing the planned shape of an intervertebral rod for attachment to implanted hardware in the spine of a subject, comprising:

a controller comprising at least a processor, a database, an input interface, an output interface, and a memory; and a robotic system, comprising a surgical robot and a robot controller; wherein the controller is adapted to:

(a) receive data relating to at least one intraoperative image comprising at least the region of the spine where the hardware has been implanted by the robotic system;

(b) detect the actual position and orientation of the implanted hardware to which the intervertebral rod is to be attached;

(c) if the detected positions and orientations of the implanted hardware components do not permit the intervertebral rod to be attached without applying more than a predetermined level of force to the rod, change the planned shape of the rod so as to facilitate attachment;

(d) determine if a rod having the changed planned shape of the intervertebral rod obtained in step (c), would, if attached to the inserted hardware, achieve a spine configuration having acceptable values of selected spinal alignment parameters;

(e) if the changed planned shape of the intervertebral rod to be inserted does not achieve acceptable values of the selected spinal alignment parameters, further change the planned shape of the rod towards achieving acceptable values of the selected spinal alignment parameters;

(f) determine if a rod having the further changed planned shape of step (f) maintains attachability to the implanted hardware;

(g) if the amended planned shape of the rod does not achieve an acceptable level of the selected spinal alignment parameters while maintaining attachability to the implanted hardware, instruct the robotic system to perform a spinal manipulation procedure on at least one vertebra of the spine of the subject; and (h) repeat steps (a) to (g) until a rod having a planned shape is obtained which, when attached to the implanted hardware, generates acceptable values of the selected spinal alignment parameters.

In implementations of the system for optimizing the planned shape of an intervertebral rod for attachment to implanted hardware in the spine of a subject, the data may be received via one of a user input interface or a network connection. The controller may be further adapted to instruct the robotic system to define the positions in the spine of the subject for implantation of the hardware. If an intervertebral rod having the planned shape provided in step (d) does not maintain compatibility with the implanted hardware, steps (b) to (e) may be repeated, such that step (g), if needed, is performed only after a predetermined number of iterations of steps (d) to (f).

According to yet a further implementation of the systems described in this disclosure, there is also provided a system for optimizing the planned shape of an intervertebral rod for attachment to implanted hardware in the spine of a subject, comprising:

a system controller comprising at least a processor, an input interface, an output interface, and a memory; and a robotic system, comprising a surgical robot and a robot controller; wherein the system controller is adapted to:

(a) receive data relating to at least one intraoperative image comprising at least the actual position and orientation of the implanted hardware to which the intervertebral rod is to be attached;

(b) if the positions and orientations of the implanted hardware components do not permit the intervertebral rod to be attached without applying more than a predetermined level of force to the rod, iteratively changing the planned shape of the rod so as to increase compatibility of the shape of the rod with the positions and orientations of the implanted hardware components, while maintaining a spine configuration having acceptable values of selected spinal alignment parameters;

(c) if, after a predetermined number of iterative changes of the planned shape of the rod, the changed planned shape of the rod does not achieve an acceptable level of the selected spinal alignment parameters while maintaining compatibility with the implanted hardware, instruct the performance of a spinal manipulation procedure on at least one vertebra of the spine of the subject; and (d) repeat steps (b) and (c) a predetermined number of times to achieve convergence towards a rod having a planned shape which, if attached to the implanted hardware, would generate acceptable values of the selected spinal alignment parameters.

In such a system, the instruction for the performance of a spinal manipulation procedure on at least one vertebra of the spine of the subject, can be directed either to the robotic controller or to a surgeon. The instructions to the surgeon may comprise a) advice that a spinal manipulation is recommended, or b) a suggestion to execute a specific spinal manipulation. The instructions to the robotic controller may comprise a) a specific spinal manipulation for the robot to perform, which the surgeon can then approve or alter, or b) direct instruction to the robotic system to perform the spinal manipulation procedure.

In this disclosure, processes, techniques, apparatus, and materials as known to one of ordinary skill in the art, may not be the subject of discussion in detail but are intended to be part of the enabling description where appropriate. For example, although exact computer code may not be listed for achieving each of the steps outlined, one of ordinary skill would be able to generate such code from the disclosure within. Such code is intended to fall within the scope of at least one embodiment.

The details of one or more aspects of the disclosure are set forth in the accompanying drawings and the description below. It is to be understood that the scope of the methods revealed in this disclosure have many more applications than is possible to describe in their entirety. One implementation is thus described in detail, with other possibilities suggested in brief. Additional features, objects, and advantages of the techniques will be apparent from the description and drawings, and from the claims.

BRIEF DESCRIPTION OF THE DRAWINGS

Embodiments of the present disclosure will be understood and appreciated more fully from the following detailed description, taken in conjunction with the drawings in which.

DETAILED DESCRIPTION

Figure 1A:
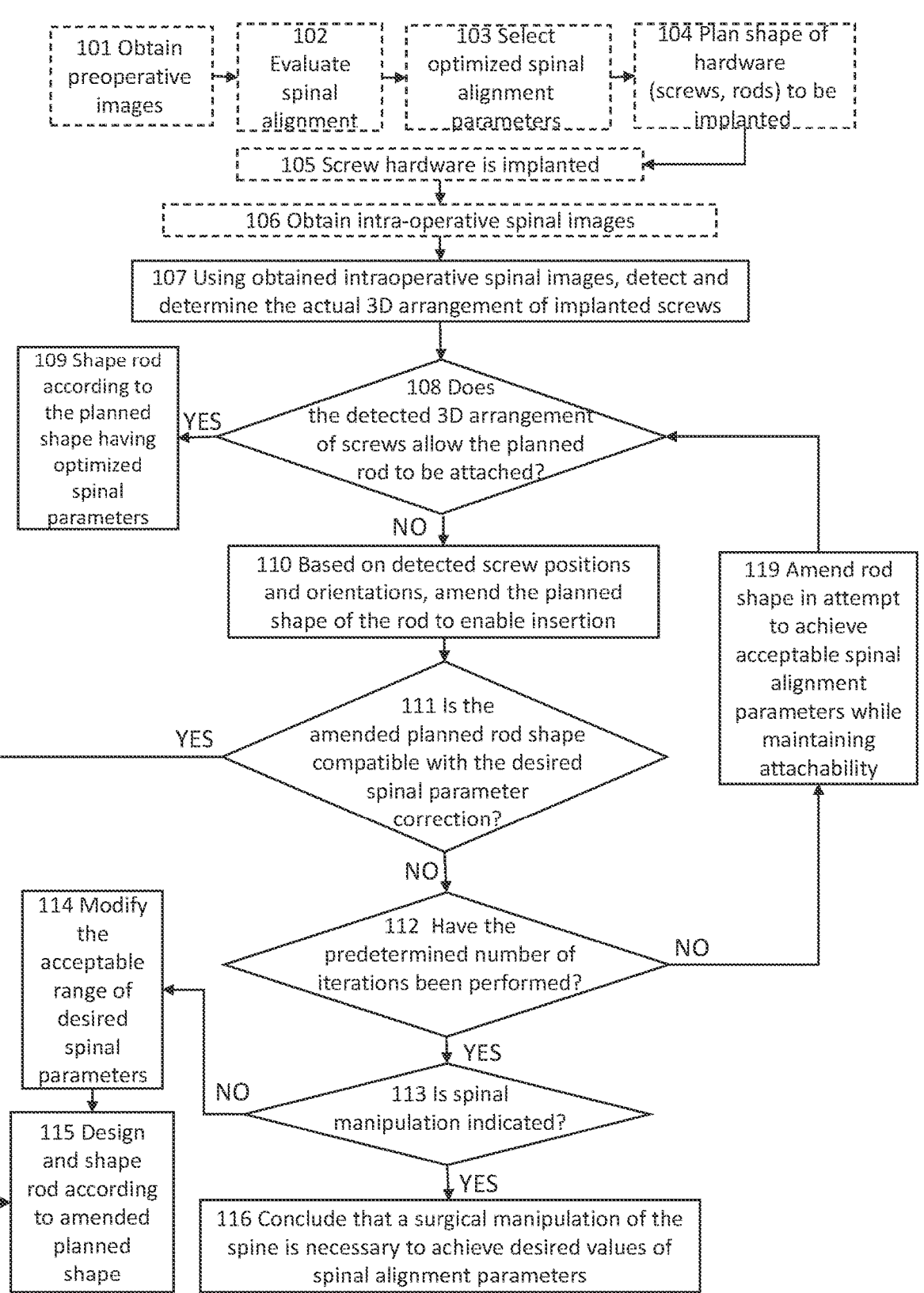
FIG. 1A shows the steps taken in an embodiment of the methods of the present disclosure, to correct the shape of a planned intervertebral rod based on actual position and orientation of implanted pedicle screws, also taking spinal alignment parameters into consideration.
Figure 1B:
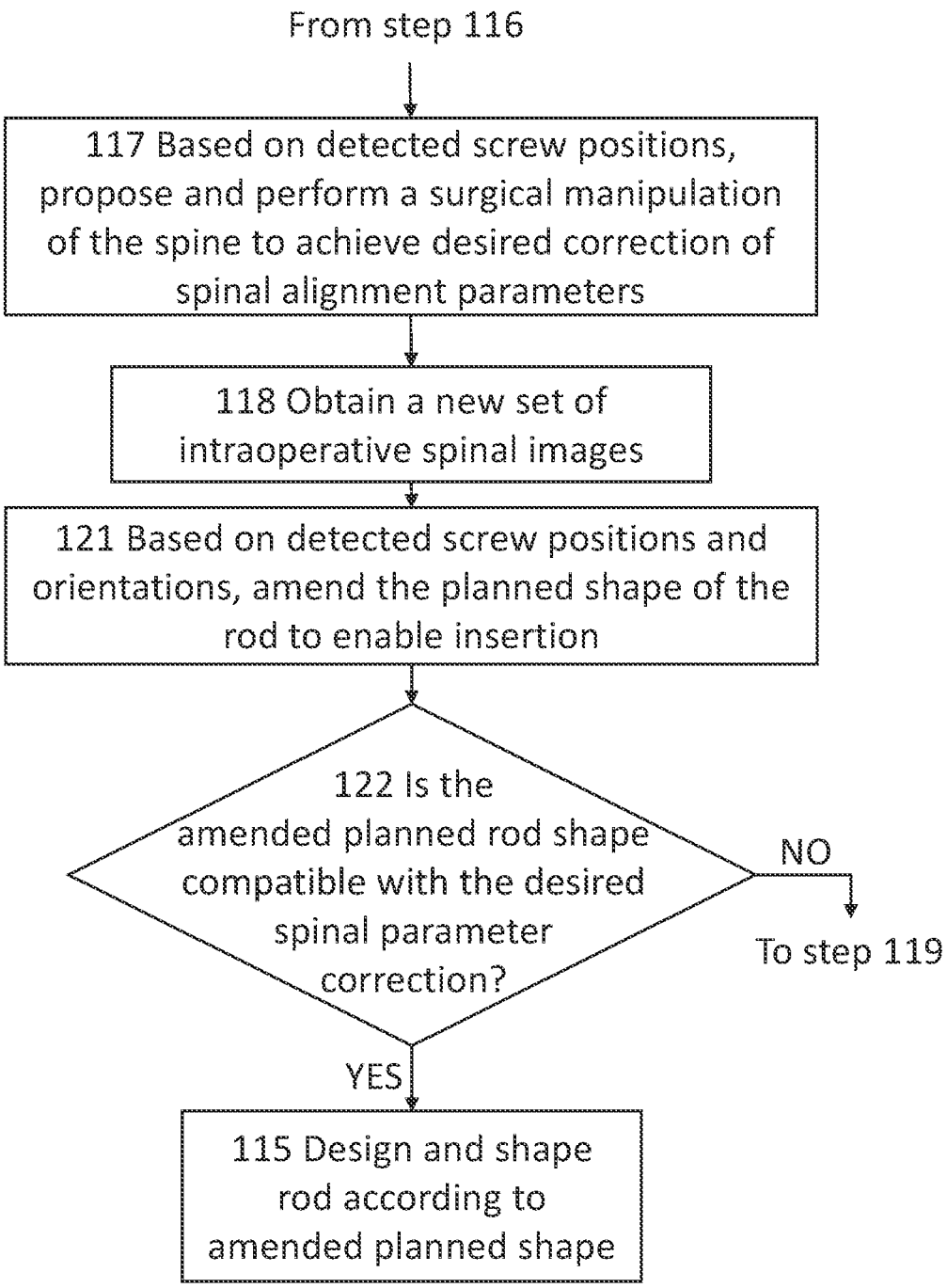
FIG. 1B shows the steps taken in another embodiment of the disclosure, to update spinal alignment parameters taking into consideration the corrected shape of a planned intervertebral rod.

Reference is now made to FIGS. 1A and 1B, which illustrate schematically the steps involved in two typical embodiments of the disclosure. Both are methods for use with an operation or procedure to correct vertebral pathology, such as scoliosis or kyphosis. In such operations, the patient presents with abnormal spinal alignment parameters, and one goal of the procedure is to correct these parameters to the degree anatomically possible. This correction is accomplished by implanting hardware, in most cases pedicle screws inserted into the vertebral pedicles and intervertebral rods bent in a shape that models the normal spinal curvature. When the rods are inserted into the tulips of the pedicle screws and the screws tightened, the resulting pressure on the vertebral column results in a degree of correction of the spinal alignment. In some cases, the optimal correction of spinal alignment parameters would place undue stress on the implanted screws and rods, potentially resulting in a pull out of the screws or breakage of the rods, and hence failure of the desired correction. Thus, a balance must be sought between the desired optimization of spinal parameters and the shape of the rod to be inserted into the implanted screws. The possibility of undue stress on the rod-screw system and the balance with alignment of spinal alignment parameters is considered in more detail hereinbelow in relation to the methods shown in FIG. 1C.

In both FIG. 1A and FIG. 1B, the disclosed method provides for optimization of the planned shape of an intervertebral rod taking into account the position of previously implanted pedicle screws or other hardware, and to achieve the desired optimized spinal alignment parameters. In FIG. 1A, if the method is unable to propose a suitable rod, meaning a rod which can be readily inserted through the inserted screws, and also provides an acceptable set of spinal alignment parameters, then the method proposes a surgical manipulation of the spine to achieve correction of the spinal alignment parameters. In FIG. 1B, the method further comprises the option of performing surgical manipulation of the spine and additional iterations of the earlier steps.

While the options presented in FIGS. 1A and 1B represent the above mentioned distinct possibilities, it is to be understood that the method is not limited to only these two scenarios. In some embodiments, the same steps may be performed in a different order, some steps may be omitted, or, if vertebral alignment is satisfactory and the operation is being performed for another reason, such as stabilization, the spinal alignment parameters may be ignored. In other cases, surgical manipulation is indicated because otherwise, the optimal rod geometry for alignment with the screw tulips would place undue stress on the bone-implant system, potentially resulting in screw pullout or failure of the fusion procedure.

In FIGS. 1A and 1B, steps 101 through 106, in dotted outlines, are carried out in sequential preoperative and intraoperative steps, in order to set up the situation at which the planning method of the present application can be executed. In step 101, preoperative images are obtained. In step 102, spinal alignment is evaluated. In step 103, a set of spinal alignment parameters is selected, if needed to provide the desired correction. In step 104, the position and shape of the rods and screws to provide that correction, are planned. In step 105, the screws are inserted. The purpose of these steps is to acquire preoperative three-dimensional images of the operative region, to evaluate spinal alignment and calculate any corrections needed to be applied intraoperatively to optimize the spinal alignment, to plan the type, number, and shape of hardware to be implanted, and to insert the screws in their intended positions. Typically, the hardware comprises a number of pedicle screws and two or more intervertebral rods to which the screws are to be connected. In a typical operation, performed either as an open operation or more advantageously, as a minimally invasive procedure, the pedicle screws are implanted first, either by the surgeon or via robotic control. Although the screws are placed according to the preoperative plan, based on intraoperative findings, the surgeon may decide to change the location or number of screws. Once the screws are inserted, the spinal column may be manipulated manually or less preferably, surgically, for example via whole or partial osteotomy, to improve the vertebral alignment.

In step 106, and before the surgeon inserts an intervertebral rod to fit within the pedicle screw heads, at least one intra-operative image is obtained of the operative region.

In step 107 of FIG. 1A, the obtained intra-operative spinal images are analyzed to detect the position and orientation of the implanted pedicle screws. The detection method may be similar to that discussed in WO 2019/102473, for "A Method for Verifying Hard Tissue Location using Implant Imaging", having a common inventor with the present application. It uses image processing based on gray levels in fluoroscopic, CT, or MRI images, with additional programming for noise reduction. The advantage of this method over, for example, a touch probe or robotic detection via a navigation system, is that the screws are identified in intra-operative images of the patient, by both actual position of the pedicle head and also by the screw's length and orientation. Accordingly, these embodiments of the present disclosure have an advantage of greater accuracy over approaches that simply rely on, e.g., a touch probe in that these embodiments detect the three-dimensional screws in their implanted locations.

In step 108, the method assesses whether the detected three-dimensional arrangement of screw heads allows the planned rod to be attached. The assessment is based on comparison of the implanted screw positions and orientations with the initially planned rod shape, to determine whether the planned rod is able to be attached to or inserted into the detected screw orientations and positions. The ability or ease of attachment of the rod to the inserted screws is determined not only by the absolute spatial position of the screw heads in relation to the rod shape, but also takes into account any force that may need to be applied to the rod or to the vertebrae onto which the rod is to be attached. In the case of the rod-applied force, the force that may be applied is selected such that the rod does not undergo the type of excessive force, that would weaken it sufficiently to endanger the long term viability of the spinal correction. In the case of the forces that may be applied to the vertebrae to ensure that the rod fits into the screw heads, such forces are selected to ensure that no physiological damage is caused, and particularly, that the joints, especially the facet joints, are not stressed to a level that would cause pain to the subject.

If it is determined that the planned rod can be attached or inserted, within the above described limitations of those terms, the method proceeds to step 109, in which the rod is shaped as planned according to the preoperative plan, or according to the surgeon's preference, this being a successful conclusion of the method. On the other hand, if in step 108, the screw arrangement does not allow the planned rod to be attached, the algorithm proceeds to step 110, in which the system amends the planned shape of the rod minimally, in an attempt to enable insertion, based on the detected screw positions and orientations. In step 110, the planned rod shape is virtually amended intraoperatively in one or more planes, according to the detected three-dimensional arrangement of the implanted screws, as detailed below. Since comparing the planned rod shape and detected screw position does not depend on preoperative images, there is no need to register the intraoperatively obtained images with the preoperative images. The method extracts the implanted position and orientation of the screws, as well as the vertebral alignment, directly from the intraoperative images. It integrates this information with the preoperatively planned rod shape to determine compatibility between the virtual, planned rod and the actual, detected screw positions and orientations. This can be achieved, for instance, by superimposing image data of the rod, onto the image data of the implanted screws from the intraoperative images of the spine with the screws implanted therein. This procedure can be repeated for every amendment of the virtual, planned rod shape generated in the planning procedure.

The purpose of the intraoperative three-dimensional image obtained in step 107 is twofold: first, to identify the actual screw position in order to make the required amendment to the planned shape of the rod in step 110. Additionally, not shown in FIG. 1A, and incidental to the main goal of the implementation described in this step, in some implementations, the surgeon may opt to compare the actual position and orientation of the screws with the position of the screws in the preoperative plan. Observing the actual position allows the surgeon to make any necessary adjustments in the procedure, as opposed to just updating the rod shape, based on unexpected anatomical findings in the images.

In step 111 of FIG. 1A, a comparison is made between the amended planned rod shape based on the detected screw positions, and the expected effect of these changes on the desired correction of spinal alignment parameters. The alignment of the vertebral column in the intraoperative images is assessed and the system decides whether the amended planned rod shape is compatible with the desired, optimized spinal parameters. If at this point of the process, no changes in the planned shape of the rod are needed, the planned rod is regarded as fulfilling the needs and goals of the spinal surgical procedure, and the system will proceed to step 115 where the rod is shaped according to the planned shape, having optimized spinal alignment parameters, and being capable of attachment to the heads of the installed screws. Step 115 therefore represents a second possible successful conclusion of the method.

Thus, if the method arrives at either of steps 109 or 115, the presently discussed implementation of the planning process has reached completion. The rod may then be shaped, such as by using the rod shaper disclosed in U.S. application Ser. No. 15/533,037, for Shaper for Vertebral Fixation Rods, co-assigned to the present applicant, or by using any other rod shaping apparatus.

On the other hand, optimization of the two parameters, i.e., rod shape and spinal alignment, may be found to have incompatible implications, in that the shape of the rod to enable attachment to the implanted pedicle screws, may not achieve acceptable correction of spinal alignment parameters. In some cases, amending the planned shape of the rod to fit the detected screw positions will negatively impact the desired correction of the spinal alignment parameters. Thus, if, in step 111, the amended planned rod shape is incompatible with the desired optimized spinal alignment parameters, the method proceeds via step 112 to step 119. In step 119, the planned shape of the rod is amended again, attempting to achieve acceptable spinal alignment parameters, while also trying to maintain attachability of the planned rod to the implanted screws, and the procedure to ascertain the suitability of the newly amended rod shape is then begun again at step 108. In this disclosure, the term attachability is used to mean, depending on the action being attempted with the rod, either the ability to attach the rod to its associated hardware using no more than a predetermined level of force to bring the attachment points of the rod and it associated hardware element into alignment, or the ability to insert the rod into the points of attachment in its associated hardware, as may be performed in a minimally invasive procedure.

However, since execution of the new amendment of the rod shape in step 119 indicates another round of an iterative process, the method must first ascertain whether the iterative process is converging or not, and this is done in step 112, by determining whether steps 108-119 have been performed through a predetermined number of iterations, that number being deemed as necessary to investigate a sufficient number of possible rod shapes for the case in hand. If the predetermined number of iterations has not been performed, the method returns from step 112 via step 119 to step 108. This process, i.e., steps 108-110-111-119, may be repeated a predetermined number of times; in step 112, if the predetermined number of iterations has been reached without finding an acceptable combination of rod shape and corrected spinal alignment parameters, the method will proceed to step 113.

In step 113, the method assesses whether manipulation of the spine is indicated to achieve acceptable spinal alignment parameters with an insertable rod. In this disclosure, use of the term 'spinal manipulation' or 'manipulation of the spine' refers to either surgical or manual manipulation steps, performed by either the surgeon or the robotic surgical system, whose net effect is intended to correct the spinal alignment parameters of the patient under treatment.

If manipulation of the spine is not indicated, the method proceeds to step 114 and the system or the surgeon modifies the acceptable range of desired spinal alignment parameters, usually by widening the acceptable range for one or more of the parameters, to accommodate the achieved amended planned rod shape. The method then proceeds to step 115 and the rod is shaped according to the most updated planned shape deriving from the latest iteration shape of step 110.

If in step 113, it is determined that spinal manipulation is required, the method proceeds to final step 116, and the system concludes that a surgical manipulation of the spine is necessary in order to achieve the desired correction of spinal alignment parameters. Determination that the rod cannot be planned to achieve both attachability and an acceptable set of spinal alignment parameters without some form of surgical manipulation of the spine, is another, though less desirable, conclusion point of the methods of FIG. 1A.

Reference is now made to FIG. 1B, which begins at the conclusion of the execution of the method of FIG. 1A, which for this example, reaches the conclusion in steps 113 and 116 that without spinal manipulation, it will not be possible to achieve an acceptable rod shape which can be attached to the implanted screws, while providing an acceptable range of spinal alignment parameters. In step 117, based on detected screw positions, a surgical manipulation of the spine is proposed and performed to achieve desired correction of spinal alignment parameters, in an attempt to correct the vertebral pathology and bring the spinal alignment parameters into an acceptable range. The proposed surgical manipulation may be based on the method disclosed in International Patent Application published as WO 2017/064719, for "Global Spinal Alignment Method", assigned to the present applicant.

In step 118, following the surgical manipulation, a new set of intraoperative spinal images is obtained.

In step 121, based on this latest set of images, the implanted screw positions and orientations are identified by the system, and if needed, the planned shape of the rod is amended to enable insertion of the rod into the screw tulips.

In step 122, the system determines whether the amended planned rod shape, which now does enable insertion into the screw heads, is also compatible with the desired correction of spinal alignment parameters. If so, the method proceeds to step 112 of FIG. 1A, and the acceptable planned rod design may then be formed. If not, in a typical embodiment, the method returns to steps 120 and 119 of FIG. 1A, and the iterative procedure of finding an acceptable rod shape for the newly aligned vertebral column of the patient after manipulation, is repeated, in order to achieve an amended rod shape with acceptable spinal alignment parameters, while ensuring that the rod remains attachable to the implanted hardware. In one embodiment (not shown) in which the rod shape has been corrected a predetermined maximal number of times, the method may return from step 121 to step 113, to ask if additional spinal manipulation is required either to allow the planned rod to be fitted to the implanted screws, or to allow the spinal alignment parameters to fall within the desired corrected range.

In some embodiments of the disclosed method, the decisions in steps 111 and 122 of determining if the amended rod shape is compatible with the desired range of spinal alignment parameters, are performed by the system controller, programmed to operate independently and make the relevant assessments, as will be explained in the implementation shown in FIG. 3 hereinbelow. However, a human operator may intervene at either of these steps, or at step 114. When the decisions are made by the system, they may be automated by incorporating machine learning or other forms of artificial intelligence. Information may be taken from databases of results from previous operations of the same type, from published articles, from calculations of screw pull out strength, Young's modulus analysis of the stress on the bent rod, or from other scientific and medical sources.

Whether the system or the surgeon performs these steps, the system operates iteratively until an amended planned rod shape is designed that meets the requirements of both being insertable or attachable to the implanted pedicle screws, and also enables acceptable correction of spinal alignment parameters. The algorithm may operate for a single rod, or for multiple rods at the same time.

In some patients, it may be that, because of vertebral pathology or other physical limitations, the amended planned rod shape from step 111 or step 118 is incompatible with the desired optimized spinal parameters, and it may not be advisable to alter the acceptable range of spinal alignment parameters in step 114. If the solutions of FIG. 1A or FIG. 1B are determined to be unsatisfactory, in a further implementation of the methods of the present disclosure, because of the difficulty in achieving an acceptable rods shape by execution of the methods of FIG. 1A or FIG. 1B, the surgeon or the system may elect to switch to an alternative computerized method illustrated in FIG. 1C.

Figure 1C:
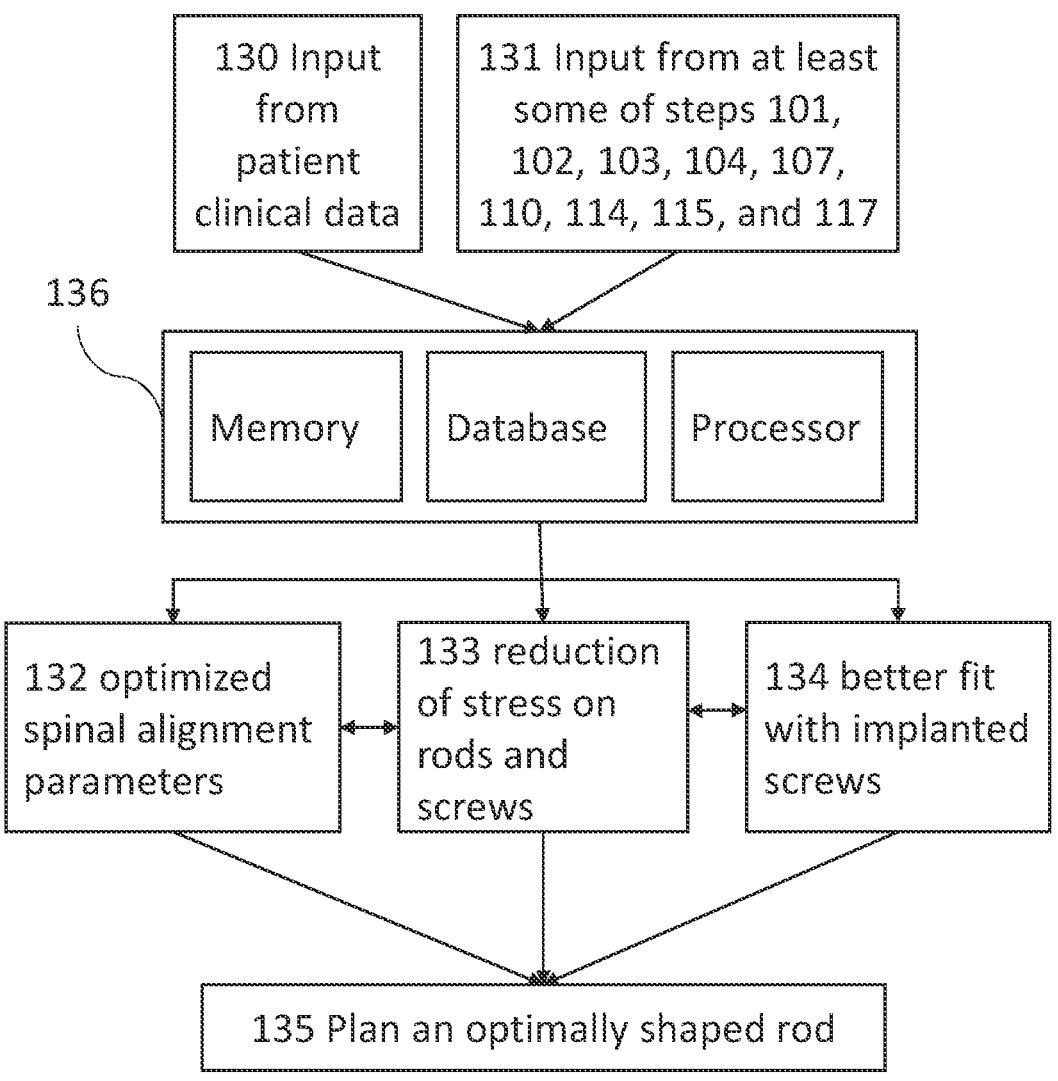
FIG. 1C illustrates schematically the steps of an alternative method for achieving an optimally shaped intervertebral rod, using biomechanical analysis, machine learning or any other form of artificial intelligence, to determine the optimal rod shape.

In FIG. 1C the method for optimizing the planned rod shape uses input from the patient's clinical data 130 and from at least some of the steps shown in the previously described methods of FIGS. 1A and 1B (primarily steps 101, 102, 103, 104, 107, 110, 114, 115, and 117). These input parameters may be analyzed, using biomechanical analysis, machine learning or any other form of artificial intelligence, in the system controller 136, in which all of the input data are processed to determine an optimal shape for the rod 135. The controller typically comprises a memory unit for storing the input data, and any intermediately stored data from databases used, and a processor on which the AI or machine learning routines are run, in order to generate the optimum rod shape fulfilling the requirements of the patient.

In some embodiments, the system may consider multiple options in a cost-benefit analysis, and the rod shape may be iteratively adjusted by the control system 136 to find an acceptable compromise between correction of the spinal parameters 132, while obtaining a rod shape that will be attachable to the implanted screws 134, and with the rod shape having the additional characteristic that its curvatures and the forces which it is intended to apply to the vertebrae to which it is attached, are such that the internal stresses are at an acceptable level 133. The control system, with or without input from the surgeon, may prioritize any of a) optimized spinal alignment parameters, b) less stress on the rod, or c) better fit with the implanted screws, according to preprogrammed instructions, or according to surgeon preference input during the procedure. Generally, the correction of the spinal alignment parameters 132 will be given the highest weighting, since spinal alignment is usually the prime object of the procedure. The reduction of stress 133 on the rods and screws may be given a high weighting in situations where the extent of spinal misalignment is high, requiring instrumentation that will provide high levels of correction, and therefore the need to withstand high forces.

Use may be made of the methods described in a number of patent applications, co-assigned to the present applicant, including WO 2018/131044 for "Dynamic Motion Global Balance"; WO 2018/131045 for "Method and Apparatus for Image-based Prediction of Post-operative Spinal Pathologies"; and International Patent Application PCT/IB2019/058798 for "Implant System Force Prediction". The final planned rod shape 135 is determined by the patient's anatomy, and by the constraints of other input parameters.

In any of the implementations of the methods described in FIG. 1A, 1B, or 1C, the system may be programmed to select the best shape of the rod, based, inter alia, on selected, weighted values of a combination of specific factors such as:

desired correction of individual or collective spinal alignment parameters, not necessarily limited to the commonly used—spinal vertical axis (SVA), lumbar lordosis (LL), thoracic kyphosis (TK), pelvic tilt (PT), pelvic incidence (PI), (PI-LL), (T1 slope);

analysis of the bending strength of the material of which the rod is composed at various radii of curvature;

artificial intelligence analysis of a database of surgical outcomes, comprising clinical data and pre-operative, intra-operative, and post-operative image sets; and whether, and what level of surgical manipulation of the spine to perform.

Each of these factors weighs on the ultimate success of the spinal correction, and optimization of each one individually may negatively impact the optimization of another. For example, additional surgical manipulation, such as osteotomies, may result in better spinal alignment parameters; however, more surgical intervention tends to weaken the spine and is more traumatic for the patient. Thus, the method first attempts to optimize the rod shape and spinal alignment parameters, as outlined in the method of FIG. 1A, without resorting to surgical manipulation. The system, or the system with input from the surgeon, must consider and optimize each factor in the final decision of how to correct the planned rod shape.

Figure 2:
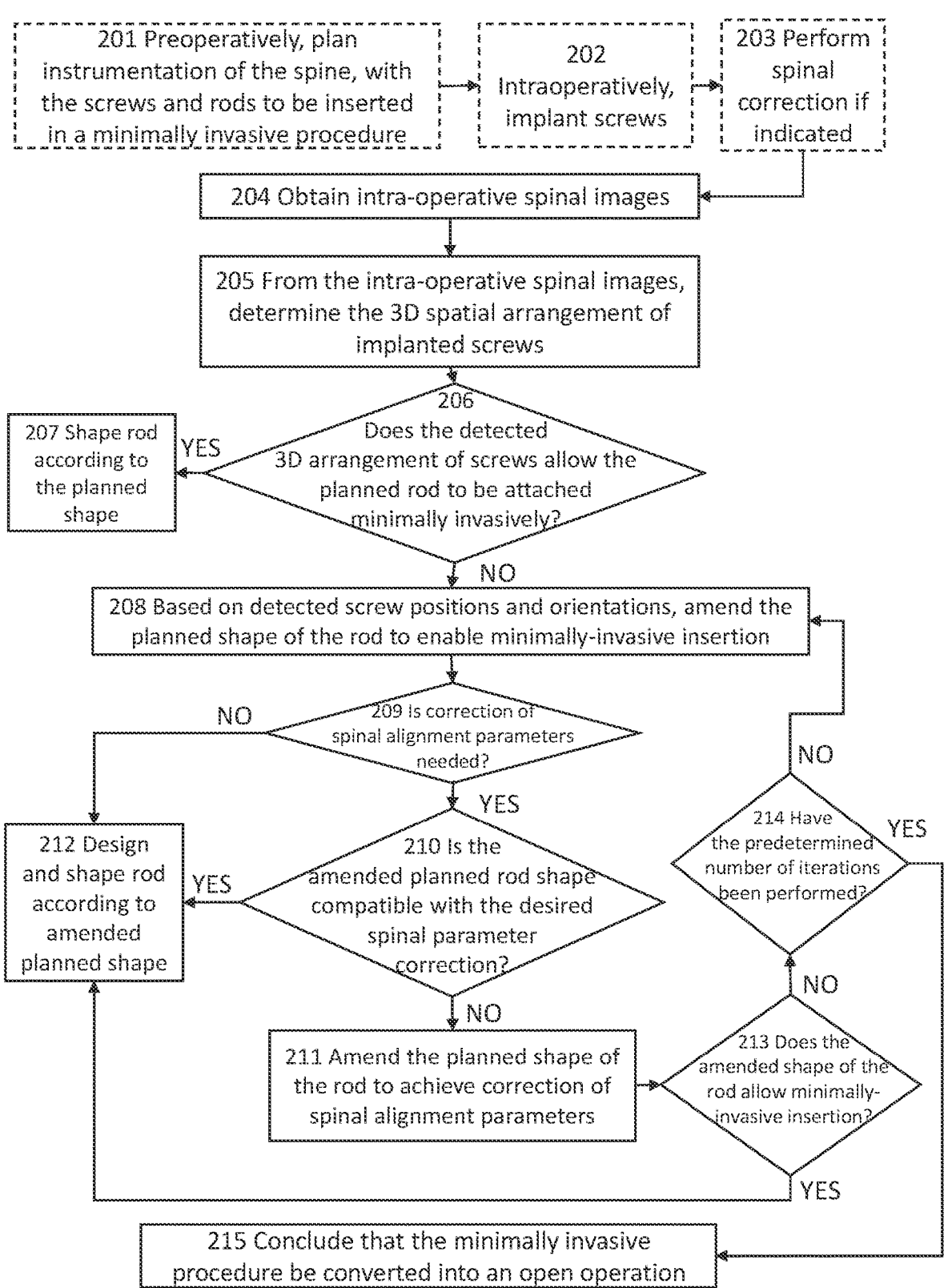
FIG. 2 shows the steps taken to correct the shape of a planned intervertebral rod based on actual position and orientation of implanted pedicle screws in a case that does not require optimization of spinal alignment parameters.

Reference is now made to FIG. 2, showing an alternative embodiment of the present disclosure for use in a procedure to be carried out in a minimally invasive manner. In this implementation, the goal of the method is to amend the planned rod shape according to the actually detected position of the implanted hardware or pedicle screw heads, which have been previously inserted minimally invasively. Apart from amending the rod shape according to the detected screw positions, a significant additional challenge in such a procedure involves designing a curved rod that may be inserted via a single opening, and is designed to pass through the tulips of the screws to which it is to be attached. Manipulating the rod may be performed by use of a robotic insertion procedure, using a motion-planning method, such as the mathematical algorithm known as the piano mover's problem. Preoperative and intraoperative steps 201-203 are carried out before the process of the current embodiment of the present disclosure is initiated.

In step 201, a preoperative plan is developed for implanting the rods and screws, taking into account the need for insertion of the hardware in a minimally invasive procedure. In step 202, the pedicle screws are inserted. In step 203, any indicated spinal manipulation may be performed. Each of steps 202 and 203 may be performed by the surgeon, or automatically via a surgical robotic system. These steps are performed prior to the steps of these methods. In step 204, intraoperative spinal images are obtained of the implanted hardware, usually pedicle screws. In step 205, the implant detection method detects and determines the three-dimensional spatial position and arrangement of the implanted screws. In step 206, these detected positions and orientations of the implanted hardware and of the vertebrae in the region of interest are compared with the planned corrections in the preoperative plan, and the system determines if the detected arrangement of the screws allows the planned rods to be inserted and attached by a minimally invasive procedure, generally from a single incision. Step 206 advantageously uses a three-dimensional motion planning program to determine if minimally invasive insertion is possible. If so, in step 207, the rod is shaped according to the preplanned shape, and can be used for the minimally invasive insertion procedure. Step 207 is therefore a first successful end-point of the procedure.

If, on the other hand, the detected screw positions do not allow the rod to be inserted minimally invasively according to the preoperative plan, this generally being the result of a rod having too tight and/or too many curves, such that it is impossible or impractical to thread it through all of the screw heads in one movement, then in step 208, an amended planned shape of the rod is created, designed to achieve a minimally invasive insertion through a single opening in the patient, and through the detected positions of the tulips of the previously inserted screws. The goal of the amended planned rod shape is to ensure that the shaped rod is generated with the most precise fit possible into the heads of the implanted screws. This will prevent having to bend the rod in a way that may either weaken it or place undue pressure on the pedicle screws, subjecting them to strain that may cause them to pull out. Either of these scenarios—a weakened rod or an overstrained screw—may result in breakage of the rods or pull out of the screws; in either case, the hardware fails, resulting in an unsuccessful spinal fusion operation.

In step 209, a determination is made as to whether the amended shape of the rod prevents achievement of spinal alignment parameter correction within a desired range of values. If not, in step 212, the rod is designed and shaped according to the directions of step 208, and may be used in the spinal correction procedure, this being a second successful end-point of the procedure. If, on the other hand, in step 209 it is determined that an acceptable level of spinal alignment parameters has not been achieved, and a corrected set of parameters is needed, the method proceeds to step 210.

In step 210, the method assesses whether the amended planned rod shape from step 208 is compatible with the desired parameter correction. If so, the method again proceeds to step 212 and a rod is designed according to the amended planed shape, and can be used for the spinal correction procedure.

During at least the first iteration of the method, it is likely that the amended planned rod shape would not be compatible with the spinal alignment parameter correction, in which case, the method proceeds to step 211 and the planned shape of the rod is amended to achieve correction of spinal alignment parameters.

In step 213, the method assesses whether the amended planned shape of the rod from step 211 allows the rod to be inserted minimally invasively. If it is determined to be insertable in a minimally invasive manner, the method again proceeds to step 212 and a rod is designed according to the amended planed shape.

If, however, the rod is found not to be insertable in a minimally invasive manner, the method continues to step 214 to determine if the preselected number of iterations has been performed. If not, the method returns to step 208 and iterations of steps 208-209-210-211-213 are performed.

In step 214, if the system determines that the predetermined maximum number of iterations have been performed, and no solution that allows both the desired correction of spinal alignment parameters and minimally invasive insertion of the rod has been found, the method proceeds to step 215. In step 215, the system concludes that a minimally invasive procedure cannot be achieved, and proposes conversion of the procedure into an open operation, which typically enables desired correction of spinal alignment parameters, and broader options for the actual inserting process of the rod into the screw tulips.

It is to be understood that the method shown in FIG. 2 is only one embodiment of the present disclosure. Other options may be exercised, for example, by reordering the sequence of specific steps, or omitting the assessment of spinal alignment parameters. In some embodiments of step 208, for instance, it may be found that it is not possible to reach a planned rod shape that is insertable in a minimally-invasive manner, in which case the method may skip directly to step 215, and an open surgical procedure is indicated.

Figure 3:
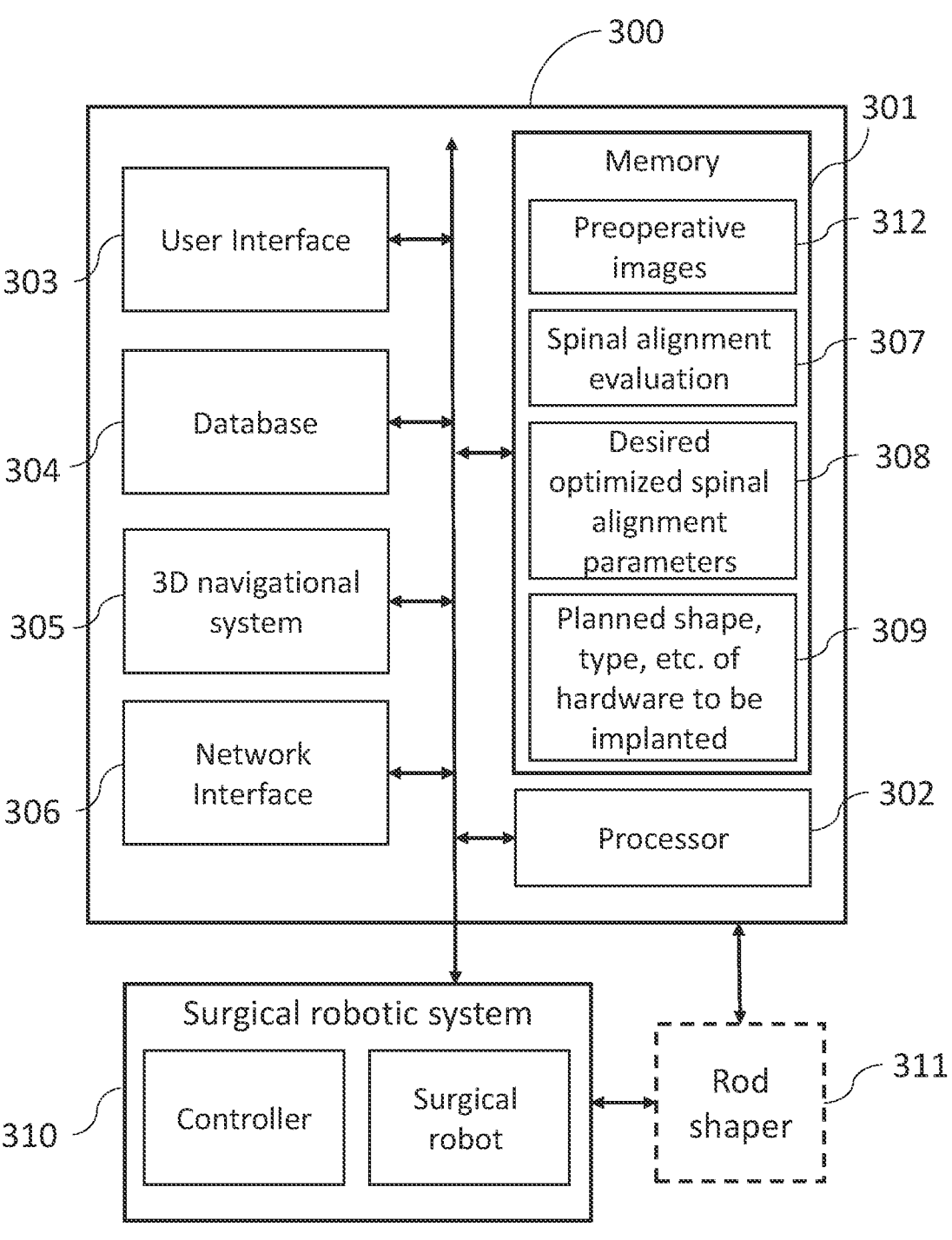
FIG. 3 shows the structure of a system for carrying out the planning methods described in FIGS. 1A, 1B, 1C and 2.

Reference is now made to FIG. 3, which is a block diagram, illustrating schematically one example of the structure of a system which may be used to implement the algorithms described in FIGS. 1A, 1B, 1C and 2. The system may comprise:

a system controller 300, inputting the relevant information, performing the rod calculations, and providing control instruction signals, which are then output to:

a surgical robotic system 310, generally comprising a robot controller and a surgical robot that carries out some or all of the steps from the preoperative plan, and optionally also:

a rod shaping machine 311, that creates the amended, planned rod shape.

The system controller 300, may comprise an interconnected user interface 303, a database 304, optionally a three-dimensional navigational system 305, and a network interface 306. A processor 302 connects with these elements, and interfaces with a memory component 301, comprising at least some of the image data of the preoperative images 312, the spinal alignment evaluation 307, the desired optimization of the spinal alignment parameters 308, and the preoperatively planned shape, size, number, and type of the implanted hardware such as pedicle screws and rods 309. The system may be attached to a surgical robotic system 310 comprising a controller and a surgical robot that carries out some or all of the steps from the preoperative plan. In some embodiments, the coordinate tracking system 305 may be a component of the system 300, whereas in other embodiments, it may be a part of the surgical robotic system 310. The system 300 and the surgical robotic system 310 may be connected to a rod shaper tool 311 that creates the amended, planned rod shape.

The rod shaper may comprise any conveniently usable system, for example, that disclosed in U.S. application Ser. No. 15/533,037, for "Shaper for Vertebral Fixation Rods", having common inventors with the present application. The system 300, 310 may enact the algorithms described in FIGS. 1A, 1B, 1C, and 2, and others not included in the present disclosure. Following the planning of an amended rod shape, in some embodiments, the rod is created intraoperatively by the rod shaper 311 and inserted or attached via the surgical robotic system 310 having robotic navigation, to increase the accuracy of rod insertion.

It is appreciated by persons skilled in the art that specific embodiments of the present disclosure are not limited by what has been particularly shown and described hereinabove. Rather the scope of the present disclosure includes both combinations and subcombinations of various features described hereinabove as well as variations and modifications thereto which would occur to a person of skill in the art upon reading the above description and which are not in the prior art.

What is claimed is:

1. A system for optimizing a planned shape of an intervertebral rod for improving selected spinal alignment parameters of a subject, the system comprising:

at least one processor executing instructions stored on at least one non-transitory storage medium, to cause the at least one processor to:

receive at least one intraoperative image comprising at least a region of a spine containing implanted hardware to which the intervertebral rod is to be attached, and, from the at least one intraoperative image, detect a position and/or orientation of the implanted hardware;

change, when the detected position and/or orientation of the implanted hardware are incompatible with the planned shape of the intervertebral rod such that the intervertebral rod cannot be attached to the implanted hardware without applying more than a predetermined level of force to at least one of the intervertebral rod and a screw to which the intervertebral rod is to be attached, the planned shape of the intervertebral rod so as to increase compatibility with the detected position and/or orientation of the implanted hardware;

determine whether the intervertebral rod having the changed planned shape achieves a spine configuration that matches values of the selected spinal alignment parameters when attached to the implanted hardware;

iteratively change, when the changed planned shape of the intervertebral rod does not match values of the selected spinal alignment parameters, the planned shape of the intervertebral rod to match values of the selected spinal alignment parameters for a predetermined number of iterations;

provide, when the planned shape of the intervertebral rod does not match the values of the selected spinal alignment parameters after the predetermined number of iterations while maintaining compatibility with the implanted hardware, a recommendation to change a range of the selected spinal alignment parameters to improve the matching between the selected spinal alignment parameters of the subject and the planned shape of the intervertebral rod; and control a surgical robot to implant a shaped intervertebral rod by at least attaching the shaped intervertebral rod to at least one component of the implanted hardware.

2. The system of claim 1, wherein changing the planned shape of the intervertebral rod is performed in at least one of a sagittal plane and a coronal plane of the spine of the subject.

3. The system of claim 1, wherein at least one planned shape of the intervertebral rod allows the shaped intervertebral rod to be attached to the at least one component of the implanted hardware by insertion through a single opening in the subject in a minimally invasive procedure.

4. The system of claim 1, wherein at least some of the implanted hardware comprises pedicle screws.

5. The system of claim 1, wherein the planned shape is changed using a path planning algorithm.

6. The system of claim 1, wherein a radius of curvature of a planned bend for the intervertebral rod is greater than a predetermined level.

7. The system of claim 6, wherein the predetermined level of the radius of curvature is determined such that a strength of the intervertebral rod does not fall below a predetermined limit.

8. The system of claim 1, wherein the selected spinal alignment parameters comprise at least one of spinal vertical axis (SVA), lumbar lordosis (LL), thoracic kyphosis (TK), pelvic tilt (PT), pelvic incidence (PI), (PI-LL), and sagittal pelvic angle (T1 slope).

9. The system of claim 1, wherein the implanted hardware comprises at least one of titanium, steel, and silicone.

10. The system of claim 1, wherein the position and/or orientation of the implanted hardware are detected using an image-processing routine.

11. The system of claim 10, wherein the image-processing routine is trained using one of machine learning or other form of artificial intelligence, and wherein the image-processing routine identifies the implanted hardware from surrounding bony tissue.

12. The system of claim 11, wherein the image-processing routine is trained continuously.

13. The system of claim 1, wherein changing the range of the selected spinal alignment parameters comprises widening the range of the selected spinal alignment parameters.

14. A system for optimizing a planned shape of an intervertebral rod to be attached to implanted hardware during a minimally invasive procedure, the system comprising:

at least one processor executing instructions stored on at least one non-transitory storage medium to cause the at least one processor to:

detect, in at least one intra-procedural image, a position and orientation of implanted hardware to which the intervertebral rod is to be attached;

determine whether the detected position and orientation of the implanted hardware permit the intervertebral rod to be inserted minimally invasively;

amend, if the detected position and orientation of the implanted hardware do not permit the intervertebral rod to be inserted minimally invasively, a planned shape of the intervertebral rod such that the intervertebral rod is configured to be inserted and attached minimally invasively;

determine if the intervertebral rod having the amended planned shape achieves a spine configuration that matches values of selected spinal alignment parameters when attached to the implanted hardware;

iteratively amend, when the amended planned shape of the intervertebral rod does not match the values of selected spinal alignment parameters, the planned shape of the intervertebral rod to match a desired spinal alignment parameter for a predetermined number of iterations;

provide, if the amended planned shape of the intervertebral rod does not allow desired correction of the selected spinal alignment parameters through a minimally invasive rod insertion procedure after the predetermined number of iterations, a recommendation to increase a range of the selected spinal alignment parameters to improve the matching between the desired spinal alignment parameter and the amended planned shape of the intervertebral rod; and control a surgical robot to implant a shaped intervertebral rod by at least attaching the shaped intervertebral rod to at least one component of the implanted hardware.

15. The system of claim 14, wherein amending or further amending the planned shape of the intervertebral rod allows the shaped intervertebral rod to be attached to the implanted hardware through a single incision.

16. The system of claim 14, wherein the implanted hardware comprises pedicle screws.

17. The system of claim 14, wherein the system further implements a path planning algorithm for determining whether the amended planned shape of the intervertebral rod permits the intervertebral rod to be inserted through a single incision.

18. The system of claim 14, wherein the recommendation to amend a surgical plan comprises converting the minimally invasive procedure into an open operation.

19. The system of claim 14, wherein the recommendation to amend a surgical plan comprises a spinal manipulation.

* * * * *